US012559483B2

(12) United States Patent
Panchal et al.

(10) Patent No.: US 12,559,483 B2
(45) Date of Patent: Feb. 24, 2026

(54) PROCESS FOR THE PREPARATION OF FLUOXASTROBIN AND INTERMEDIATES THEREOF

(71) Applicant: UPL LTD, Mumbai (IN)

(72) Inventors: Digishkumar Manubhai Panchal, Mumbai (IN); Pareshkumar Kalyanji Tandel, Mumbai (IN)

(73) Assignee: UPL LTD, Mumbai (IN)

( * ) Notice: Subject to any disclaimer, the term of this patent is extended or adjusted under 35 U.S.C. 154(b) by 639 days.

(21) Appl. No.: 18/008,715

(22) PCT Filed: Jun. 8, 2021

(86) PCT No.: PCT/IB2021/055016
§ 371 (c)(1),
(2) Date: Dec. 7, 2022

(87) PCT Pub. No.: WO2021/250558
PCT Pub. Date: Dec. 16, 2021

(65) Prior Publication Data

US 2023/0219940 A1 Jul. 13, 2023

(30) Foreign Application Priority Data

Jun. 8, 2020 (IN) ............................ 202021024007

(51) Int. Cl.

*C07D 413/12* (2006.01)
*C07C 67/307* (2006.01)
*C07D 239/30* (2006.01)

(52) U.S. Cl.
CPC .......... *C07D 413/12* (2013.01); *C07C 67/307* (2013.01); *C07D 239/30* (2013.01)

(58) Field of Classification Search
CPC .... C07D 413/12; C07D 239/30; C07C 67/307
See application file for complete search history.

(56) References Cited

U.S. PATENT DOCUMENTS

| | | | | |
|---|---|---|---|---|
| 6,103,717 | A | 8/2000 | Heinemann et al. | |
| 9,193,698 | B2 * | 11/2015 | Hindupur ............. | C07D 413/12 |
| 2008/0114196 | A1 | 5/2008 | Kutschera et al. | |
| 2015/0011753 | A1 * | 1/2015 | Hindupur ............. | C07D 413/12<br>544/65 |

FOREIGN PATENT DOCUMENTS

| | | | |
|---|---|---|---|
| CN | 108658871 | A | 10/2018 |
| JP | 2002128735 | A | 5/2002 |
| WO | 0172719 | A1 | 10/2001 |
| WO | 2015006203 | A1 | 1/2015 |
| WO | 2016193822 | A1 | 12/2016 |

OTHER PUBLICATIONS

Shore, Tetrahedron Letters, vol. 56, 2015, 4063-4066. (Year: 2015).*
International Search Report and Written Opinion for International Application PCT/IB2021/055016; International Filing Date: Jun. 8, 2021; Date of Mailing: Aug. 23, 2021; 10 pages.

* cited by examiner

*Primary Examiner* — D Margaret Seaman
(74) *Attorney, Agent, or Firm* — CANTOR COLBURN LLP

(57) ABSTRACT

The invention provides an improved process for the preparation of fluoxastrobin and intermediates thereof. The present invention provides a process for the preparation of fluoaxastrobin, 4,6-dichloro-5-fluoro-pyrimidine and diethyl 2-chloromalonate that are substantially free of unwanted impurities.

21 Claims, 3 Drawing Sheets

Figure 1: GC chromatogram of Example 2

| Peak# | Ret.Time | Area | Area % |
|---|---|---|---|
| 1 | 1.309 | 979392 | 3.9832 |
| 2 | 2.999 | 22663 | 0.0922 |
| 3 | 7.938 | 78255 | 0.3183 |
| 4 | 8.941 | 3085 | 0.0125 |
| 5 | 9.810 | 69933 | 0.2844 |
| 6 | 9.886 | 4490 | 0.0182 |
| 7 | 10.133 | 22590477 | 91.8751 |
| 8 | 11.246 | 825969 | 3.3593 |
| 9 | 12.337 | 6766 | 0.0275 |
| 10 | 13.222 | 7211 | 0.0293 |
| Total | | 24588251 | 100.0000 |

Figure 2: GC chromatogram of Example 5

| Peak# | Ret.Time | Area | Area% |
|---|---|---|---|
| 1 | 4.226 | 98873 | 0.2486 |
| 2 | 5.395 | 162429 | 0.4084 |
| 3 | 6.746 | 3833 | 0.0096 |
| 4 | 7.121 | 18285 | 0.0460 |
| 5 | 8.014 | 561491 | 1.4120 |
| 6 | 9.867 | 15198 | 0.0382 |
| 7 | 9.901 | 4330 | 0.0109 |
| 8 | 10.189 | 31794335 | 79.9531 |
| 9 | 11.308 | 7107484 | 17.8732 |
| Total | | 39766249 | 100.0000 |

Figure 3: GC chromatogram of Example 8

| Peak# | Ret.Time | Area | Area% |
|---|---|---|---|
| 1 | 6.51 | 28896 | 0.0619 |
| 2 | 7.26 | 767210 | 1.6489 |
| 3 | 8.17 | 45554224 | 97.6423 |
| 4 | 9.83 | 279850 | 0.5998 |
| 5 | 12.46 | 22093 | 0.0474 |
| Total | | 46652133 | 100.0000 |

PROCESS FOR THE PREPARATION OF FLUOXASTROBIN AND INTERMEDIATES THEREOF

CROSS REFERENCE TO RELATED APPLICATIONS

This application is a National Stage application of PCT/IB2021/055016, filed Jun. 8, 2021, which claims priority to Indian Patent Application number 202021024007, filed Jun. 8, 2020, both of which are incorporated by reference in their entirety herein.

FEILD OF INVENTION

The present invention provides a process for the preparation of strobilurin compounds and intermediates thereof. More particularly the present invention provides a process for the preparation of fluoxastrobin and intermediates thereof that are substantially free of impurities.

BACKGROUND OF THE INVENTION

Fluoxastrobin is a widely used strobilurin type of broad-spectrum fungicide. It is used against fungal diseases such as leaf spots, early and late blight, and leaf rust.

Fluoxastrobin inhibits respiration within the mitochondria (energy-producing organelles in the cell), blocking the electron transfer in the respiratory chain.

Synthesis of fluoxastrobin is a multistep process. U.S. Pat. No. 6,103,717 discloses halogenopyrimidines compounds such as fluoxastrobin, process for preparing those compounds, and their use as pesticides.

One of the known methods starts with the preparation of diethyl 2-chloromalonate by the chlorination of diethyl malonate. It has been observed that the preparation of diethyl 2-chloromalonate using chlorinating agents such as sulfuryl chloride leads to the formation of a mixture of corresponding mono-chloro and dichloro compounds.

JP2002128735 discloses synthesis of chloromalonic acid diester particularly diethyl chloromalonate by chlorination of diethyl malonate using chlorine gas in presence of toluene solvent. However, it has been noted that the reaction leads to the formation of diethyl dichloro malonate in significant amounts.

Formation of diethyl dichloro malonate in the reaction mixture in the first step of the synthesis leads to quite a lot of side reactions and formation of several unwanted side products in various quantities. Such complex reaction mixtures lead to the formation of final product fluoxastrobin in poor quality and yield. Further it was extremely difficult to isolate pure fluoxastrobin from the reaction mixture.

Fluoxastrobin can only be isolated by complicated separation methods in such cases. Therefore, there is a need to develop an economic and commercially viable process for the preparing of fluoxastrobin and intermediates thereof in good yield and high purity. The present invention thus provides a process for preparation of fluoxastrobin and its intermediates substantially free from unwanted impurity.

OBJECTS OF THE INVENTION

It is an object of the present invention to provide an improved process for preparation of dialkyl-2-chloromalonate.

It is another object of the present invention to provide a process for the preparation of intermediates useful for the preparation of fluoxastrobin.

It is another object of the present invention to provide a process for the preparation of fluoxastrobin that is economical and environment friendly.

It is yet another object of the present invention to provide diethyl 2-chloromalonate that is substantially free of certain impurities.

SUMMARY OF THE INVENTION

In an aspect the present invention provides a process for the preparation of compound of formula (1) comprising:

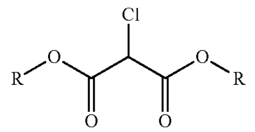

(1)

chlorinating compound of formula (2)

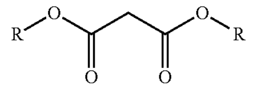

(2)

with chlorine wherein the concentration of reactive chlorine in the reaction medium during the reaction is between 0.01 to 5 mol %/minute and wherein R=$C_1$-$C_4$ alkyl.

In another aspect the present invention provides a process for the preparation of 4,6-dichloro-5-fluoro-pyrimidine of formula (5) comprising:

(i) chlorinating compound of formula (2)

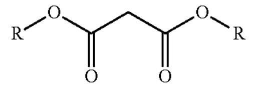

(2)

with chlorine wherein the concentration of reactive chlorine in the reaction medium is between 0.01 to 5 mol %/minute to get compound of formula (1)

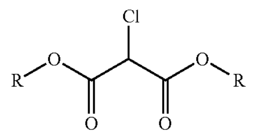

(1)

optionally without isolating compound of formula (1);

(ii) fluorinating compound of formula (1) with a fluorinating agent to get compound of formula (3)

(3)

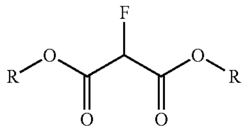

optionally without isolating compound of formula (3);

(iii) reacting compound of formula (3) with formamide or its derivative compound to get compound of formula (4);

(4)

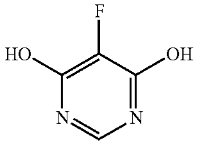

optionally without isolating compound of formula (4); and (iv) chlorinating compound of formula (4) with a chlorinating agent to get 4,6-dichloro-5-fluoro-pyrimidine of formula (5) wherein R is same as defined above.

(5)

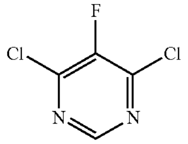

In another aspect the present invention provides a process for the preparation of fluoxastrobin of formula (9) comprising:

(i) condensing 4,6-dichloro-5-fluoro-pyrimidine of formula (5) with 2-chlorophenol of formula (6)

(6)

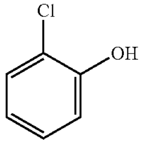

to get 4-chloro-6-(2-chlorophenoxy)-5-fluoro-pyrimidine of formula (7); and (7)

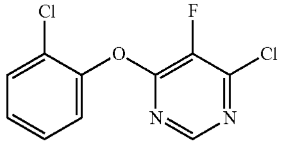

(ii) condensing 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8).

(8)

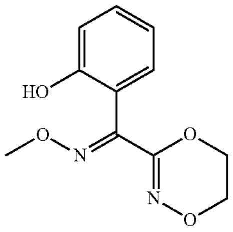

to get fluoxastrobin of formula (9)

(9)

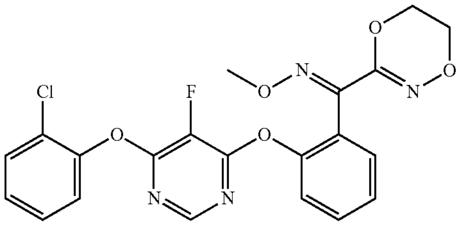

wherein said 4,6-dichloro-5-fluoro-pyrimidine of formula (5) is prepared by a process according to the present invention.

In another aspect the present invention provides a compound of formula (1), 4,6-dichloro-5-fluoro-pyrimidine of formula (5) and fluoxastrobin of formula (9) that is substantially free of dihalo malonate impurity of formula (10)

(10)

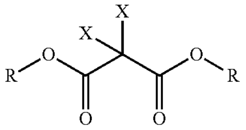

wherein X is independently selected from chlorine or fluorine and wherein compound of formula (1) wherein R═$C_1$-$C_4$ alkyl is prepared by a process according to the present invention.

In another aspect the present invention provides a process for preparation of a compound of formula (1), 4,6-dichloro-5-fluoro-pyrimidine of formula (5) and fluoxastrobin of formula (9) that is substantially free of dihalo malonate impurity of formula (10), wherein R is as defined above.

These particular aspects of the invention are not meant to be limiting, and other embodiments and aspects of the invention exist as indicated below.

DETAILED DESCRIPTION OF INVENTION

Figure 1:
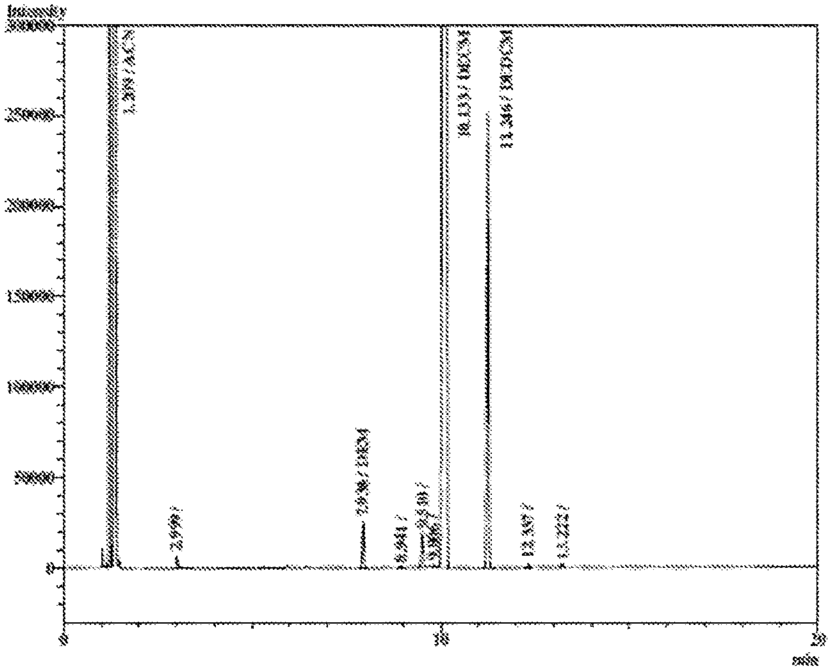
FIG. 1 represents Gas chromatography of pure diethyl 2-chloromalonate prepared according to present invention.

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of materials/ingredients used in the specification are to be understood as being modified in all instances by the term “about”. The term “about” shall be interpreted to mean “approximately” or “reasonably close to” and any statistically insignificant variations therefrom.

Thus, before describing the present invention in detail, it is to be understood that this invention is not limited to particularly exemplified systems or process parameters that may of course, vary. It is also to be understood that the terminology used herein is for the purpose of describing particular embodiments of the invention only and is not intended to limit the scope of the invention in any manner. The use of examples anywhere in this specification including examples of any terms discussed herein is illustrative only, and in no way limits the scope and meaning of the invention or of any exemplified term. Likewise, the invention is not limited to various embodiments given in this specification.

It must be noted that, as used in this specification, the singular forms “a,” “an” and “the” include plural referents unless the content clearly dictates otherwise. The terms “preferred” and “preferably” refer to embodiments of the invention that may afford certain benefits, under certain circumstances.

As used herein, the terms “comprising” “including,” “having,” “containing,” “involving,” and the like are to be understood to be open-ended, i.e., to mean including but not limited to.

The term “substantially pure” means the compound produced according to present invention is highly pure having less than about 10%, preferably less than about 5%, of undesired compounds/impurities.

The present invention provides an efficient and economical process for the preparation of the compound of Formula (I) in high purity and excellent yield.

While following general reactions conditions for preparing compound of formula (1) the reactions ended up in large quantity of dihalo malonate impurity of formula (10). Due to the similarity in the chemical nature of compound of formula (1) and dihalo malonate impurity of formula (10) wherein X=Cl, it requires complicated isolation procedures for removing dihalo malonate impurity of formula (10). A compound of formula (5) or a compound of formula (9) that is prepared from a compound of formula (1) having dihalo malonate impurity of formula (10) lead to a more complex reaction mixture that is unsuitable for adopting to prepare a compound of formula (5) or a compound of formula (9) in a commercial scale.

The present inventors have surprisingly and unexpectedly found that compound of formula (1) can be prepared in commercially viable process by chlorination of compound of formula (2) wherein the concentration of reactive chlorine in the reaction medium is between 0.01 to 5 mol % per minute. Thus, present invention provides a process for preparation of compound of formula (1) in high yield and purity that is substantially free from dihalo malonate impurity of formula (10).

Hereunder described are the embodiments of the present invention in detail.

According to the present invention, there is provided a process for the preparation of strobilurin compounds of Formula (9?) and intermediate compounds useful for preparation of compounds of formula (I) that is commercially viable and effective for large scale production.

Particularly the present invention provides a process for preparation of fluoxastrobin and intermediates thereof. The process for preparation of fluoxastrobin according to the present invention is represented in scheme 1 given below.

Scheme 1

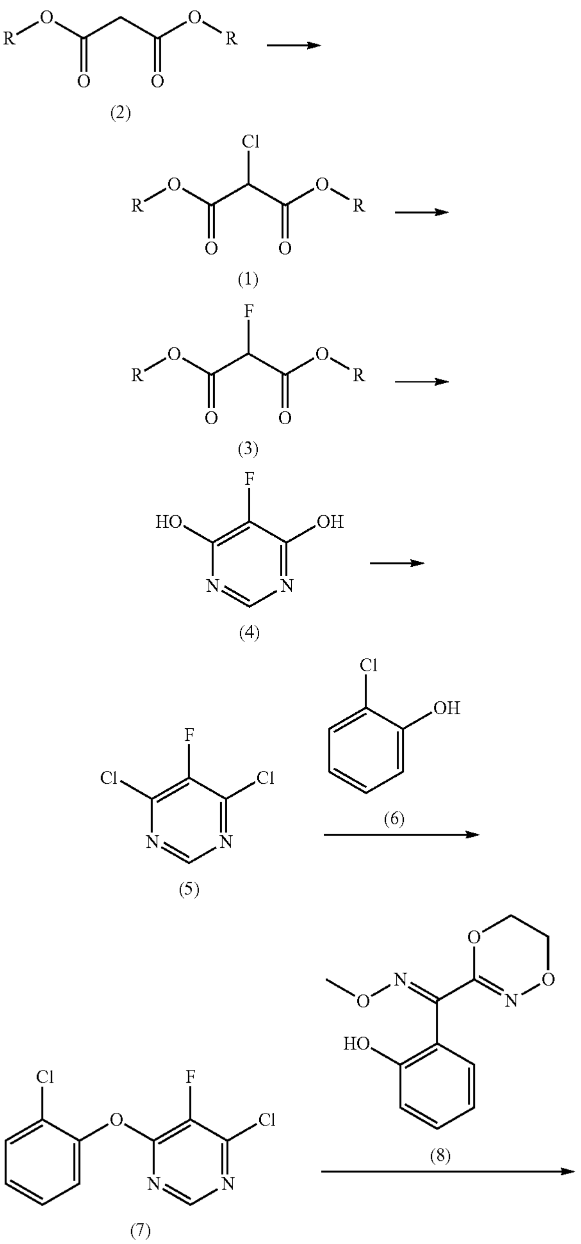

(2) (1) (3) (4) (5) (6) (7) (8)

-continued

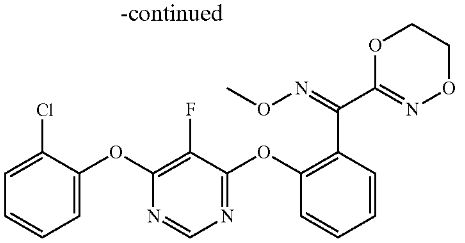

(9)

The present invention provides a process for the preparation of fluoxastrobin via the intermediate of formula (1):

(1)

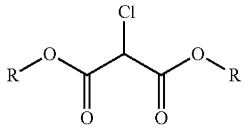

wherein the intermediate of formula (1) is prepared by chlorinating a compound of formula (2)

(2)

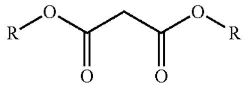

with chlorine wherein the concentration of reactive chlorine in the reaction medium during the reaction is between 0.01 to 5 mol %/minute and wherein R=$C_1$-$C_4$ alkyl.

The present invention provides a process for the preparation of compound of formula (1) comprising:

(1)

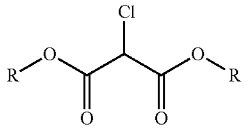

chlorinating compound of formula (2)

(2)

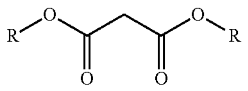

with chlorine wherein the concentration of reactive chlorine in the reaction medium during the reaction is between 0.01 to 5 mol %/minute and wherein R=$C_1$-$C_4$ alkyl.

The present invention further provides a process for the preparation of compound of formula (1) optionally comprising alkyl nitrile as a diluent.

In an embodiment, the present invention provides a process for preparing compound of formula (1) wherein R is selected from methyl, ethyl etc.

In an embodiment, the compound of formula (2) is dimethyl malonate or diethyl malonate.

In an embodiment the chlorination is performed by purging chlorine gas.

In an embodiment the concentration of reactive chlorine in the reaction medium during the reaction is between 0.01 to 5 mol % per minute.

In an embodiment the concentration of reactive chlorine in the reaction medium during the reaction is between 0.1 to 3 mol % per minute.

In an embodiment the concentration of reactive chlorine in the reaction medium during the reaction is between 0.3 to 1.5 mol % per minute.

In an embodiment the reaction is carried out in a time period of 1 to 6 hours.

In an embodiment the reaction is carried out at a temperature between 5 to 20° C.

In an embodiment the reaction is carried out at a temperature between 8 to 15° C.

In an embodiment the process for the preparation of compound of formula (1) optionally comprises alkyl nitrile as a diluent.

In an embodiment the diluent is selected from acetonitrile, propionitrile or butyronitrile.

The present invention provides a process for the preparation of 4,6-dichloro-5-fluoro-pyrimidine of formula (5) via the intermediate of formula (1)

(1)

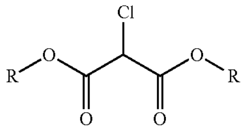

wherein the intermediate of formula (1) is obtained by chlorinating a compound of formula (2)

(2)

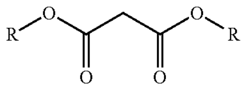

with chlorine wherein the concentration of reactive chlorine in the reaction medium during the reaction is between 0.01 to 5 mol %/minute.

The present invention also provides a process for the preparation of fluoxastrobin via 4,6-dichloro-5-fluoro-pyrimidine of formula (5)

(1)

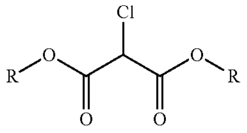

wherein the compound of formula (5) is prepared via the intermediate of formula (1), said intermediate of formula (1) being obtained by chlorinating a compound of formula (2)

(2)

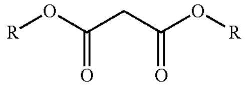

with chlorine wherein the concentration of reactive chlorine in the reaction medium during the reaction is between 0.01 to 5 mol %/minute.

The present invention provides a process for the preparation of 4,6-dichloro-5-fluoro-pyrimidine of formula (5) comprising:

(i) chlorinating a compound of formula (2)

(2)

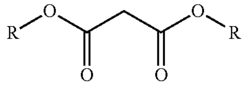

with chlorine wherein the concentration of reactive chlorine in the reaction medium during the reaction is between 0.01 to 5 mol %/minute to get compound of formula (1);

(1)

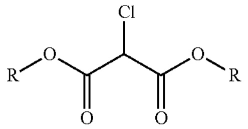

optionally without isolating compound of formula (1);

(ii) fluorinating the compound of formula (1) with a fluorinating agent to get a compound of formula (3); and (3)

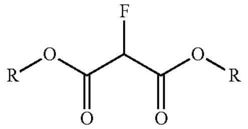

optionally without isolating compound of formula (3);

(iii) reacting the compound of formula (3) with formamide or its derivatives to get a compound of formula (4);

(4)

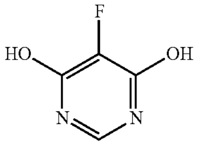

optionally without isolating compound of formula (4); and chlorinating the compound of formula (4) with a chlorinating agent to get 4,6-dichloro-5-fluoro-pyrimidine of formula (5)

(5)

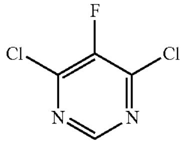

wherein R is same as defined above.

In the context of the present invention, the term "optionally" when used in reference to any step of the process; including a process step for example isolation of a compound; it is intended to mean that the subject element is isolated, or alternatively, is not isolated before converting into the further compound. Both alternatives are intended to be within the scope of the present invention.

In an embodiment, the present invention provides a process for preparing compound of formula (1) wherein R is selected from methyl, ethyl etc.

In an embodiment, the compound of formula (2) is selected from dimethyl malonate or diethyl malonate.

In an embodiment the step (ii) of the process is carried out without isolating the compound of formula (1).

In an embodiment fluorination of compound of formula (2) is performed using a fluorinating agent to get compound of formula (3) where R is same as defined above.

(3)

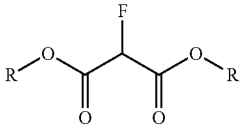

In a preferred embodiment the process according to the present invention provides compound of formula (3) wherein R is selected from methyl, ethyl etc.

In an embodiment the fluorinating agent is selected from triethyl amine trihydrofluoride, hydrofluoric acid, pyridinium poly(hydrogen fluoride), Pyridinium, 1-fluoro-2,4,6-trimethyl-, 1,1,1-trifluoromethanesulfonate (1:1) and HF complexes.

In an embodiment the reaction is performed in the presence of a base.

In an embodiment the reaction is performed in the presence of an inorganic base or an organic base.

In the above embodiment the inorganic base is selected from metal carbonate, metal bicarbonates, metal hydroxide, metal alkoxide etc.

In the above embodiment the organic base is selected from tertiary amines, pyridine, triethylamine, substituted or unsubstituted bicyclic amines etc.

In an embodiment the step (iii) of the process is carried out without isolating the compound of formula (3).

In an embodiment the compound of formula (3) is reacted with formamide or its derivatives to get a compound of formula (4);

(4)

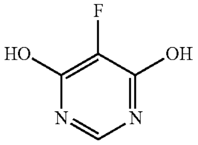

In an embodiment the reaction is performed in the presence of an alcohol/alkoxide mixture.

In an embodiment the alcohol/alkoxide mixture is selected from methanol/sodium methoxide, ethanol/sodium ethoxide and butanol/sodium butoxide.

In an embodiment the compound of formula (4) is chlorinated using a chlorinating agent to get 4,6-dichloro-5-fluoro-pyrimidine of compound of formula (5)

(5)

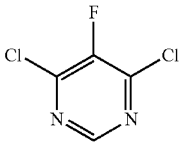

In an embodiment the chlorinating agent used for preparing the compound of formula (5) is phosphorus oxychloride.

In an embodiment the chlorination of compound of formula (4) is performed in the presence of an organic base.

In an embodiment the base is selected from dimethyl aniline, diethyl aniline, triethyl amine, tributylamine etc.

In an embodiment the molar ratio of base to phosphorus oxychloride is from 0.005 to 0.05, preferably from 0.008 to 0.1.

The present invention provides a process for the preparation of fluoxastrobin of formula (9) comprising:

(i) condensing 4,6-dichloro-5-fluoro-pyrimidine of formula (5) with 2-chlorophenol of formula (6)

(6)

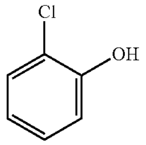

(5)

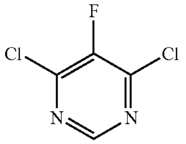

to get 4-chloro-6-(2-chlorophenoxy)-5-fluoro-pyrimidine of formula (7); and (7)

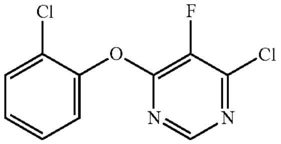

(ii) condensing 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8).

(8)

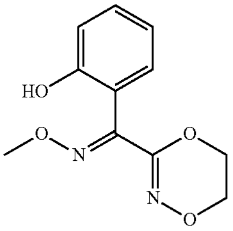

to get fluoxastrobin of formula (9)

(9)

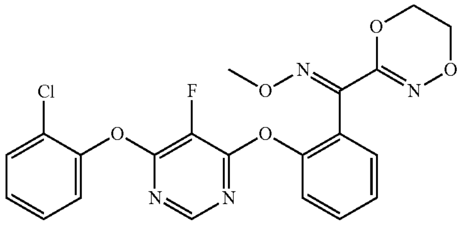

Fluoxastrobin of formula (9) obtained according to the process of the present invention is substantially free of other impurities and has chemical purity of more than 99.5%.

Fluoxastrobin as prepared according to the present invention includes its salts, solvate, a stereoisomer, or a geometrical isomer, N-oxide or polymorph thereof.

In an embodiment 4-chloro-6-(2-chlorophenoxy)-5-fluoro-pyrimidine of formula (7) is prepared by condensing 4,6-dichloro-5-fluoro-pyrimidine of formula (5) with 2-chlorophenol of formula (6)

(6)

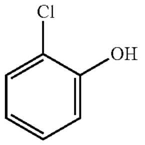

(5)

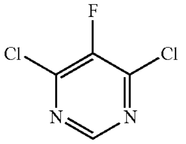

(7)

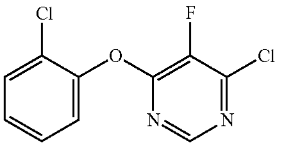

wherein said 4,6-dichloro-5-fluoro-pyrimidine of formula (5) is prepared by a process according to the present invention.

In an embodiment the condensation reaction of 4,6-dichloro-5-fluoro-pyrimidine of formula (5) with 2-chlorophenol of formula (6) is carried out in the presence of an inorganic base.

In a preferred embodiment the base is potassium carbonate.

In an embodiment the condensation reaction of 4,6-dichloro-5-fluoro-pyrimidine of formula (5) with 2-chlorophenol of formula (6) is carried out in an organic solvent.

In a preferred embodiment the solvent is methyl isobutyl ketone.

The compounds 2-chlorophenol of formula (6) and 4-chloro-6-(2-chlorophenoxy)-5-fluoro-pyrimidine of formula (7) can be prepared by known methods in the literature.

In an embodiment fluoxastrobin of formula (9) is prepared by condensing 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8).

(8)

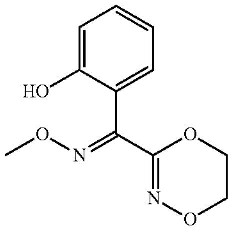

(9)

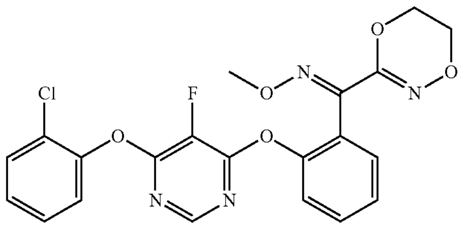

wherein said compound of formula (8) is prepared from 4,6-dichloro-5-fluoro-pyrimidine of formula (5) prepared by a process according to the present invention.

In an embodiment the condensation reaction of 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8) is carried out in the presence of an inorganic base.

The compound of formula (7) can be prepared by known method as disclosed in WO200172719.

In a preferred embodiment the inorganic base is potassium carbonate.

In an embodiment the condensation reaction of 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8) is carried out in an organic solvent, water or mixtures thereof.

In a preferred embodiment the organic solvent is methyl isobutyl ketone.

In another preferred embodiment the solvent is mixture of water and methyl isobutyl ketone.

In an embodiment the condensation reaction of 4-chloro-6-(2-chlorophenoxy)-5-fluoro-pyrimidine of formula (7) with (E)-(5,6-dihydro-1,4,2-dioxazin-3-yl)(2-hydroxyphenyl)methanone O-methyl oxime of formula (8) is carried out in the presence of a catalyst.

In an embodiment the catalyst is selected from 1,4-diazabicyclo[2.2.2]octane (DABCO) or salts or derivatives thereof, 1,8-diazabicyclo[5.4.0]undec-7-ene, salts and derivatives thereof, 1,5-diazabicyclo[4.3.0]non-5-ene salts and derivatives thereof or 1,5,7-triazabicyclo[4.4.0]dec-5-ene, salts or derivatives thereof.

The compound (E)-(5,6-dihydro-1,4,2-dioxazin-3-yl)(2-ydroxyphenyl)methanone O-methyl oxime of formula (8) can be prepared by known methods in the literature.

Preferably the intermediate compound of formula (8) is prepared by a process as disclosed in US201562168196. The entire disclosure of US201562168196 including specification, claims and summary is incorporated herein by reference in its entirety.

The present invention provides a process for preparing fluoxastrobin of formula (9) wherein a key intermediate 4,6-dichloro-5-fluoro-pyrimidine of formula (5) is prepared by a process comprising:

(i) chlorinating compound of formula (2)

(2)

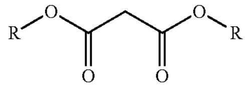

with chlorine wherein the concentration of reactive chlorine in the reaction medium during the reaction is between 0.01 to 5 mol %/minute to get compound of formula (1)

(1)

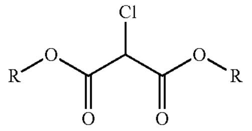

optionally without isolating compound of formula (1);

(ii) fluorinating compound of formula (1) with a fluorinating agent to get compound of formula (3)

(3)

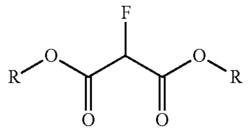

optionally without isolating compound of formula (3);

(iii) reacting compound of formula (3) with formamide or its derivatives to get compound of formula (4);

(4)

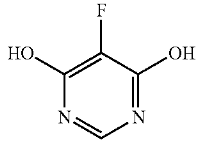

optionally without isolating compound of formula (4); and (iv) chlorinating compound of formula (4) with a chlorinating agent to get 4,6-dichloro-5-fluoro-pyrimidine of formula (5) wherein R is same as defined above.

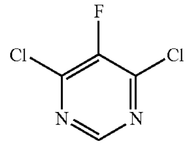
(5)

In an embodiment, the present invention provides a compound of formula (1) that is substantially free of dichloro malonate impurity of formula (10a) as characterized in FIG. 1.

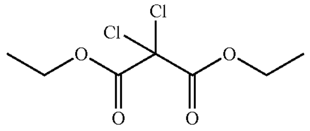
(10a)

In an embodiment, of the present invention provides a compound of formula (1) which contains less than 5% of dichloro malonate impurity of formula (10a).

In an embodiment, the present invention provides 4,6-dichloro-5-fluoro-pyrimidine of formula (5) that is substantially free of dichloro malonate impurity of formula (10a) or difluoro malonate impurity of formula (10b).

In an embodiment, of the present invention provides a compound of formula (5) which contains less than 5% of dichloro malonate impurity of formula (10a) or difluoro malonate impurity of formula (10b)

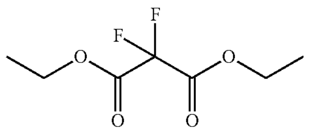
(10b)

In an embodiment, the present invention provides fluoxastrobin of formula (9) that is substantially free of dichloro malonate impurity of formula (10a) or difluoro malonate impurity of formula (10b).

In an embodiment the present invention provides a compound of formula (1) wherein R is selected from $C_1$-$C_4$ alkyl by chlorinating a compound of formula (2) using chlorine wherein the concentration of reactive chlorine in the reaction medium during the reaction is between 0.01 to 5 mol % per minute and wherein compound of formula (1) contains less than 5% of dichloro malonate impurity of formula (10a).

The advantages and other parameters of the present invention is illustrated by the below given examples. However, the scope of the present invention is not limited by the examples in any manner. It will be appreciated by any person skilled in this art that the present invention includes aforesaid examples and further can be modified and altered within the technical scope of the present invention.

EXAMPLES

Example 1: Preparation of Diethyl 2-Chloromalonate

Chlorine (95 g, 1.33 moles) is purged at a rate of 1.05 g/min (1.19 mole %/min) in a solution of diethyl malonate (200 g, 1.25 moles) in acetonitrile (600 g) at 10-15° C. for 1.5 hours and the resulting mixture is maintained at same temperature for 30 minutes. Nitrogen gas is purged in the reaction mixture for 1 h followed by solvent recovery by distillation under reduced pressure to obtain 250 g of the diethyl 2-chloromalonate. [Purity by GC: 92.91%, 1,3-diethyl 2,2-dichloropropanedioate: 3.88%].

Example 2: Preparation of Diethyl 2-Chloromalonate

Chlorine (95 g, 1.33 moles) is purged at a rate of 0.63 g/min (0.71 mole %/min) in a solution of diethyl malonate (200 g, 1.25 moles) in acetonitrile (600 g) at 10-15° C. for 2.5 hours and the resulting mixture is maintained at same temperature for 30 minutes. Nitrogen gas is purged in the reaction mixture for 1 h followed by solvent recovery by distillation under reduced pressure to obtain 250 g of diethyl 2-chloromalonate. [Purity by Gas Chromatography: 91.87%, 1,3-diethyl 2,2-dichloropropanedioate: 3.36% (FIG. 1)].

Example 3: Preparation of Diethyl 2-Chloromalonate

Chlorine (77 g, 1.084 moles) is purged 0.85 g/min (1.2 mol %/min) to a solution of diethyl malonate (160 g, 1.00 moles) in acetonitrile (480 g) at 15-20° C. for 1.5 hours and the resulting mixture is maintained at same temperature for 30 minutes. Nitrogen gas is purged in the reaction mixture for 1 h followed by solvent recovery by distillation under reduced pressure to obtain 197 g of diethyl 2-chloromalonate. [Purity by GC: 92.83%, 1,3-diethyl 2,2-dichloropropanedioate: 3.73%].

Example 4: Preparation of Diethyl 2-Chloromalonate

Chlorine (303 g, 4.26 moles) is purged 3.19 g/min (1.123 mol %/min) to a solution of diethyl malonate (640 g, 4.00 moles) in acetonitrile (1920 g) at 15-20° C. for 95 minutes and the resulting mixture is maintained at same temperature for 30 minutes. Nitrogen gas is purged in the reaction mixture for 1 h followed by solvent recovery by distillation under reduced pressure to obtain 800 g of diethyl 2-chloromalonate. [Purity by GC: 93.68%, 1,3-diethyl 2,2-dichloropropanedioate: 3.8%].

Example 5

Preparation of Diethyl 2-chloromalonate (Comparative Example)

Figure 2:
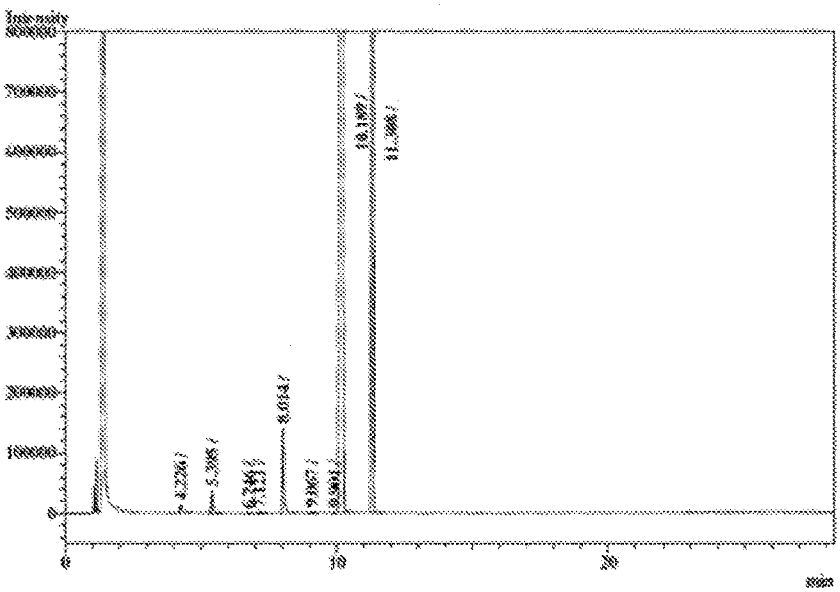
FIG. 2 represents Gas chromatography of diethyl 2-chloromalonate prepared according to example 5 (comparative example).

Sulfuryl chloride (160 g, 1.19 moles) is slowly added to a solution of diethyl malonate (160 g, 1.00 moles) at 35-40° C. in 90 minutes and the resulting mixture is maintained at same temperature for 60 minutes. Nitrogen gas is purged in the reaction mixture for 1 h to obtain 200 g of diethyl 2-chloromalonate. [purity by GC: 79.95%, 1,3-diethyl 2,2-dichloropropanedioate: 17.87%, (FIG. 2)].

Example 6

Preparation of Diethyl 2-chloromalonate (Comparative Example)

Chlorine (4.0 g, 0.05 moles) is purged into a solution of diethyl malonate (96.1 g) in toluene (166 g), and the mixture is heated to 60° C. This solution is stirred for 10 minutes, and after confirming the progress of the reaction, chlorine gas (54.0 g, 0.760 moles) is further bubbled in at room temperature for 3 hours. After stirring for a further 1 hour, water (90 g) is added. The organic layer is separated and first washed with a 6.3% aqueous sodium hydrogen carbonate solution (160 g) & then with water (50 g) and finally with saturated brine (60 g). Toluene is distilled off from organic layer by distillation to obtain 123 g of diethyl 2-chloromalonate. [purity by GC: 65.63%, 1,3-diethyl 2,2-dichloropropanedioate: 13.40%].

Example 7: Preparation of Diethyl 2-Fluoromalonate

To a mixture of diethyl 2-chloromalonate (prepared in Example 4) (400 g, 2.00 moles) in triethylamine (300 g, 2.97 moles) is added drop-wise triethylamine tri(hydrogen fluoride) (198 g, 1.23 moles) at room temperature The reaction mixture is then heated to 100-105° C. for 18-20 hours at atmospheric. The reaction mixture is cooled to room temperature and diluted with toluene (410 ml) and water (410 ml). The aqueous layer is separated and extracted with toluene (220 ml). The combined organic layer is washed with water (220 ml). The organic layer is distilled under reduced pressure and the product is fractionally distilled to obtain 200 g diethyl 2-fluoromalonate.

Example 8: Preparation of Diethyl 2-Fluoromalonate

Figure 3:
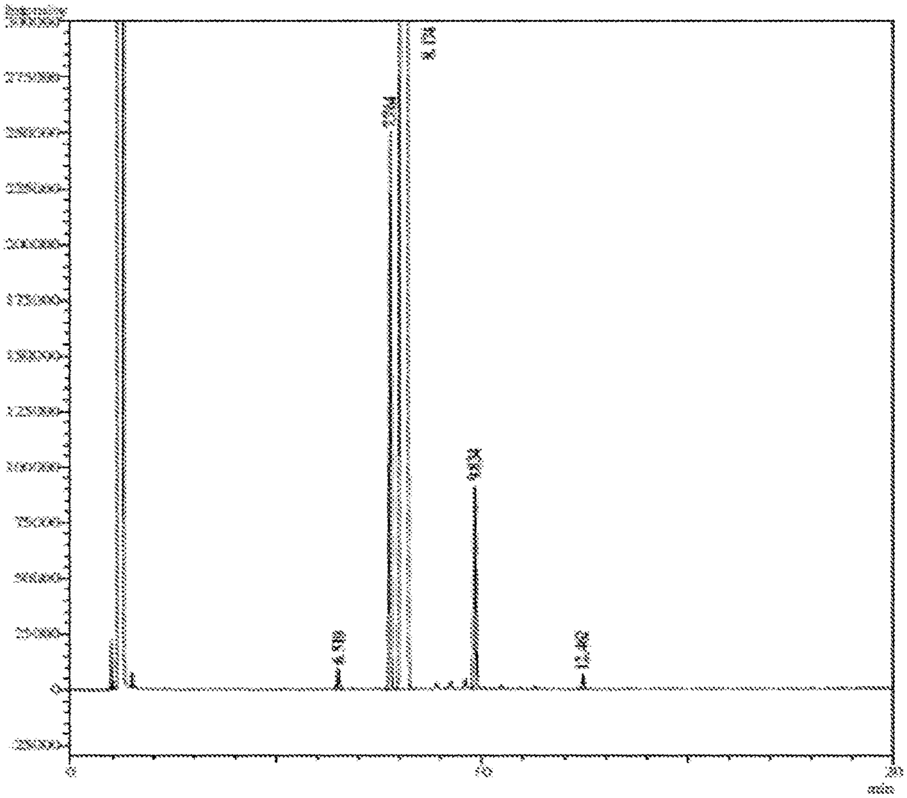
FIG. 3 represents Gas chromatography of diethyl 2-fluoromalonate prepared according to present invention.

To a mixture of diethyl 2-chloromalonate (805 g, 3.84 moles) in triethylamine (600 g, 5.93 moles) is added drop-wise triethylamine tri(hydrogen fluoride) (395 g, 2.45 moles) at room temperature The reaction mixture is then heated to 105-110° C. for 18-20 hours under pressure (4-5 kg) in an autoclave. The reaction mixture is cooled to room temperature and diluted with toluene (865 ml) and water (865 ml). The aqueous layer is separated and extracted with toluene (432 ml). The combined organic layer is washed with water (432 ml). The organic layer is distilled under reduced pressure and the product is fractionally distilled to obtain 402 g diethyl 2-fluoromalonate. [Purity by GC: 97.64%, 1,3-diethyl 2,2-difluoropropanedioate: less than 0.05% (FIG. 3)].

Example 9: Preparation of 4,6-dihydroxy-5-fluoropyrimidine

Sodium methoxide powder (189 g, 3.50 mole) is slowly added to methanol (441 g) under nitrogen atmosphere. The solution is heated to 80-85° C. To this solution is added the diethyl 2-fluoromalonate (178.16 g, 1.0 moles) in formamide (225 g, 5.0 moles) in 3 to 4 hours under reflux. The reaction is maintained under reflux for 1 hour. Methanol is distilled under reduced pressure. The reaction mixture is poured in water (438 g). The mixture is acidified with concentrated HCl to pH 1-2. The solid thus obtained is filtered, washed and dried to obtain 110 g of 4,6-dihydroxy-5-fluoropyrimidine. [Purity by HPLC: 96.21%].

Example 10: Preparation of 4,6-dichloro-5-fluoropyrimidine

To a stirred mixture of phosphorus oxychloride (1194 g, 7.77 moles) and N,N-dimethyl aniline (9.42 g, 0.077 moles) is lot-wise added 4,6-dihydroxy-5-fluoropyrimidine (Purity: 96.2%, 210 g, 1.55 moles) and the resulting mixture is heated to 95-110° C. and stirred for 2 hours. The reaction is cooled to 90-95° C. and phosphorus trichloride (428 g, 3.11 moles) is added to the reaction mixture with simultaneous purging of chlorine gas (221 g, 3.11 moles) and continued stirring for 5 hours. Phosphorus oxychloride is recovered, and the reaction mixture is cooled to room temperature. Methylene dichloride (400 9 m) is added to the reaction mixture and it is quenched with chilled water (400 gm). Aqueous layer is extracted with methylene dichloride (200 gm) and the combined organic layer is washed with water (200 gm). The organic layer is azeotrope to remove water, recover MDC & distilled product to obtain 218 g of 4,6-dichloro-5-fluoropyrimidine. [Purity by GC: 97.46%].

Example 11: Preparation of Fluoxastrobin

A solution of (E)-(5,6-dihydro-1,4,2-dioxazin-3-yl)(2-hydroxyphenyl)methanone O-methyl oxime (476 g, 2.0 moles) and DABCO (10 g, 0.089 moles) in water (800 ml) is added to a solution of 4-chloro-6-(2-chlorophenoxy)-5-fluoropyrimidine (518 g, 2.0 moles) in methyl isobutyl ketone (1000 ml). To this mixture, potassium carbonate (372 g, 2.69 moles) is added. The mixture is heated to 70° C. for 3 hours. Water is added to the hot mixture and layers are separated. The organic phase is distilled. The mixture is cooled to 20° C. Methanol is added to precipitate the product. The suspension is cooled to 5° C., filtered, washed with methanol and dried to give fluoxastrobin (855 g).

We claim:

1. A process for the preparation of fluoxastrobin via the intermediate of formula (1), or via the intermediate of formula (5) prepared via the intermediate of formula (1):

(1)

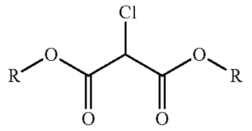

(5)

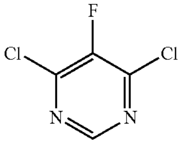

wherein the intermediate of formula (1) is prepared by chlorinating a compound of formula (2):

(2)

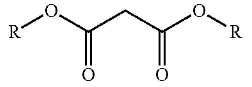

with chlorine, wherein the concentration of reactive chlorine in the reaction medium during the reaction is between 0.01 to 5 mol %/minute and wherein R=$C_1$-$C_4$ alkyl, wherein the reaction is carried out at a temperature in a range of 5 to 20° C. for a period of 1 to 6 hours.

2. The process for the preparation of fluoxastrobin, as claimed in claim 1, via the intermediate of formula (1):

(1)

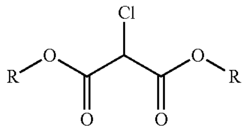

wherein the intermediate of formula (1) is prepared by chlorinating a compound of formula (2)

(2)

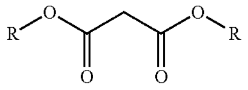

with chlorine, wherein the concentration of reactive chlorine in the reaction medium during the reaction is between 0.01 to 5 mol %/minute and wherein R=C1-C4 alkyl.

3. The process for the preparation of fluoxastrobin according to claim 1, via 4,6-dichloro-5-fluoro-pyrimidine of formula (5) comprising:

(5)

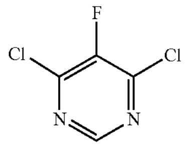

wherein the compound of formula (5) is prepared via the intermediate of formula (1), said intermediate of formula (1) being obtained by chlorinating a compound of formula (2)

(1)

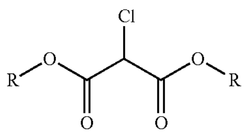

(2)

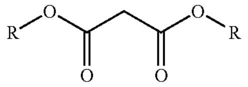

with chlorine, wherein the concentration of reactive chlorine in the reaction medium during the reaction is between 0.01 to 5 mol %/minute.

4. A process for the preparation of a 4,6-dichloro-5-fluoro-pyrimidine of formula (5) comprising:

(5)

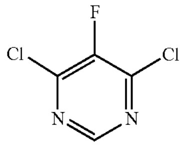

via the intermediate of formula (1)

(1)

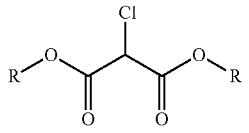

wherein the intermediate of formula (1) is obtained by chlorinating a compound of formula (2)

(2)

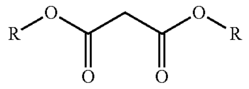

with chlorine, wherein the concentration of reactive chlorine in the reaction medium during the reaction is between 0.01 to 5 mol %/minute.

5. A process for the preparation of a compound of formula (1) comprising:

chlorinating a compound of formula (2)

(2)

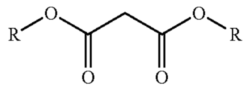

with chlorine, wherein the concentration of reactive chlorine is in the range of 0.01 to 5 mol %/minute and wherein R=C1-C4 alkyl.

6. The process according to claim 5, wherein the compound of formula (2) is dimethyl malonate or diethyl malonate.

7. The process according to claim 5, wherein the chlorination reaction is carried out using chlorine gas.

8. The process according to claim 5, wherein the concentration of reactive chlorine in the reaction medium during the reaction is between 0.1 to 3 mol % per minute.

9. The process according to claim 5, wherein the reaction is carried out in the presence of a diluent.

10. The process according to claim 9, wherein said diluent is an alkyl nitrile selected from acetonitrile, propionitrile or butyronitrile.

11. The process according to claim 1, wherein said compound of formula (1) is substantially free of the dihalo malonate impurity of formula (10)

(10)

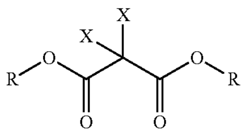

wherein X is independently selected from chlorine and fluorine.

12. A process for preparation of a 4,6-dichloro-5-fluoro-pyrimidine of formula (5) comprising:

(i) chlorinating a compound of formula (2)

(2)

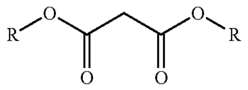

with chlorine, wherein the concentration of reactive chlorine is between 0.01 to 5 mol %/minute to provide a compound of formula (1) substantially free of dihalo malonate impurity of formula (10)

(1)

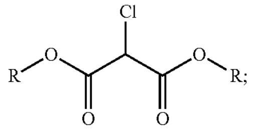

(ii) treating the compound of formula (1) with a fluorinating agent to get a compound of formula (3)

(3)

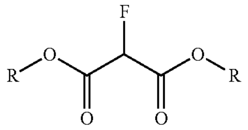

wherein R=C1-C4 alkyl;

(iii) reacting the compound of formula (3) with formamide or its derivatives to provide a compound of formula (4);

(4)

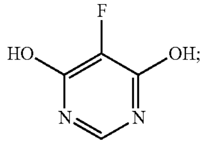

and (iv) treating the compound of formula (4) with a chlorinating agent to provide the 4,6-dichloro-5-fluoro-pyrimidine of formula (5)

(5)

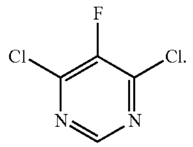

13. The process according to claim 12, wherein in the step (ii) said fluorinating agent is selected from triethyl amine trihydrofluoride, hydrofluoric acid, pyridinium poly(hydrogen fluoride), pyridinium, 1-fluoro-2, 4, 6-trimethyl-, 1,1,1-trifluoromethanesulfonate (1:1), and HF complexes.

14. The process according to claim 12, wherein the fluorination reaction in step (ii) is carried out in the presence of inorganic base or organic base.

15. The process according to claim 14, wherein said inorganic base is selected from metal carbonates, metal bicarbonates, metal hydroxides, and metal alkoxides, and said organic base is selected from tertiary amines, pyridine, triethylamine, and substituted or unsubstituted bicyclic amines.

16. The process according to claim 12, wherein the step (iii) reaction is performed in the presence of an alcohol/alkoxide mixture.

17. The process according to claim 16, wherein said alcohol/alkoxide mixture is selected from methanol/sodium methoxide, ethanol/sodium ethoxide, and butanol/sodium butoxide.

18. The process according to claim 12, wherein the chlorinating agent in step (iv) is phosphorus oxychloride.

19. The process according to claim 12, wherein step (iv) is performed in the presence of an organic base selected from dimethyl aniline, diethyl aniline, triethyl amine, and tributyl amine.

20. The process according to claim 12, wherein the molar ratio of organic base to phosphorus oxychloride in step (iv) is 0.005 to 0.05.

21. The process according to claim 12, further comprising converting the compound of formula (5) to fluoxastrobin of formula (9) by:

(i) condensing the 4,6-dichloro-5-fluoro-pyrimidine of formula (5) with 2-chlorophenol of formula (6)

(6)

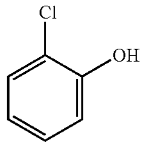

to provide 4-chloro-6-(2-chlorophenoxy)-5-fluoro-pyrimidine of formula (7); and (7)

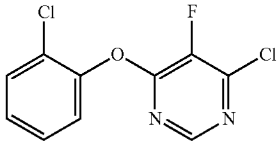

(ii) condensing 4-chloro-6-(2-chlorophenoxy)-5-fluoropyrimidine of formula (7) with 2-[5,6-dihydro-1,4,2-dioxazin-3-yl-(methoxyamino)methyl]phenol of formula (8)
(8)
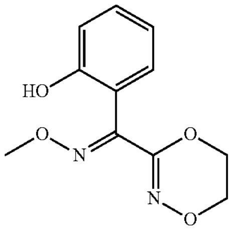
to provide fluoxastrobin of formula (9)
(9)
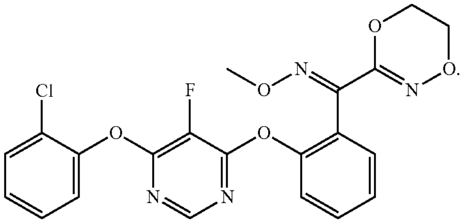
* * * * *